(12) United States Patent
Chao et al.

(10) Patent No.: US 8,772,194 B2
(45) Date of Patent: Jul. 8, 2014

(54) METHOD FOR PREPARING LARGE-SIZED TITANIUM-SILICALITE MOLECULAR SIEVE AND METHOD FOR PREPARING CYCLOHEXANONE OXIME USING THE MOLECULAR SIEVE

(75) Inventors: Shih-Yao Chao, Taipei (TW); Cheng-Fa Hsieh, Taipei (TW); Chien-Chang Chiang, Taipei (TW); Ya-Ping Chen, Taipei (TW); Pin-To Yao, Taipei (TW)

(73) Assignee: China Petrochemical Development Corporation, Taipei (Taiwan), Taipei (TW)

( * ) Notice: Subject to any disclaimer, the term of this patent is extended or adjusted under 35 U.S.C. 154(b) by 88 days.

(21) Appl. No.: 13/344,869

(22) Filed: Jan. 6, 2012

(65) Prior Publication Data

US 2012/0209029 A1    Aug. 16, 2012

(30) Foreign Application Priority Data

Feb. 14, 2011    (TW) .............................. 100104712 A

(51) Int. Cl.
*B01J 29/89* (2006.01)
*C07C 249/04* (2006.01)

(52) U.S. Cl.
USPC ........... 502/242; 502/172; 502/158; 502/232; 502/200; 564/267

(58) Field of Classification Search
USPC .................. 502/158, 172, 200, 232, 242
See application file for complete search history.

(56) References Cited

U.S. PATENT DOCUMENTS

| | | | |
|---|---|---|---|
| 4,410,501 A | 10/1983 | Taramasso et al. | |
| 5,500,199 A | 3/1996 | Bellussi et al. | |
| 6,106,803 A | 8/2000 | Hasenzahl et al. | |
| 6,524,984 B2 | 2/2003 | Carati et al. | |
| 2004/0152583 A1* | 8/2004 | Grosch et al. ................. | 502/38 |

OTHER PUBLICATIONS

Wang et al., "Preparation of titanium silicalite-1 catalytic films and applications as catalytic membrane reactors", Chemical Engineering Journal, No. 156, pp. 562-570 (2010).
Li et al., "The synthesis and characterization of titanium silicalite-1", Journal of Materials Science, vol. 37, pp. 1959-1965 (2002).
Gamba et al., "TS-1 from First Principles", J. Phys. Chem. A, vol. 113, pp. 15006-15015 (2009).
Zhang et al., "Hydrothermal Synthesis of Titanium Silicalite-1 Structurally Directed by Hexamethyleneimine", Ind. Eng. Chem. Res., vol. 48, pp. 4334-4339 (2009).

* cited by examiner

*Primary Examiner* — Samantha Shterengarts
*Assistant Examiner* — Amanda L Aguirre
(74) *Attorney, Agent, or Firm* — Edwards Wildman Palmer LLP; Peter F. Corless; Mark D. Russett

(57) ABSTRACT

The present invention provides a method for preparing a large-sized titanium-silicalite molecular sieve, and a method for preparing cyclohexanone oxime using the large-sized titanium-silicalite molecular sieve. The method for preparing a large-sized titanium-silicalite molecular sieve includes preparing a mixture of a titanium source, a silicon source and a template agent; heating the mixture to form a gel mixture; mixing a colloidal silica with the gel mixture; heating the gel mixture mixed with the colloidal silica in a water bath; and calcining the gel mixture mixed with the colloidal silica. In the present invention, the average particle size of the large-sized titanium-silicalitem molecular sieve is more than 10 um, and the particle size distribution is centralized, so as to avoid the formation of titanium-oxygen-titanium bonding. The method for preparing cyclohexanone oxime using the large-sized titanium-silicalite molecular sieve results in high conversion rate, high selectivity and easy recovery.

16 Claims, 4 Drawing Sheets

METHOD FOR PREPARING LARGE-SIZED TITANIUM-SILICALITE MOLECULAR SIEVE AND METHOD FOR PREPARING CYCLOHEXANONE OXIME USING THE MOLECULAR SIEVE

CROSS-REFERENCES TO RELATED APPLICATIONS

This application claims under 35 U.S.C. §119(a) the benefit of Taiwanese Application No. 100104712, filed Feb. 14, 2011, the entire contents of which is incorporated herein by reference.

BACKGROUND OF THE INVENTION

1. Field of the Invention

The present invention relates to a method for preparing a titanium-silicalite molecular sieve, and more particular to, a method for preparing a large-sized titanium-silicalite molecular sieve with high reactivity and a method for preparing a cyclohexanone oxime using the large-sized titanium-silicalite molecular sieve.

2. Description of the Prior Art

Crystalline titanium-silicalite molecular sieves are formed by incorporating titanium into the zeolite structure of silicon dioxide, and have the MFI structures, which are also named as the TS-1 molecular sieves. U.S. Pat. No. 4,410,501 discloses the preparation of this molecular sieve. Such molecular sieve is used as a catalyst in an oxidation reaction, wherein hydrogen peroxide is used as an oxidant. However, the hydrolysis rate of the titanium source is too fast to match the hydrolysis rate of the silicon source, such that the two materials may not mixed evenly, and the order degree of the material is decreased. Moreover, the titanium source may become anatase, and the catalyst is thus degraded. Therefore, it is important to have even mixing of materials and proper hydrolysis rates of the titanium source and the silicon source, and to avoid the formation of anatase.

Chemical Engineering Journal 156 (2010) 562-570, Journal of Materials Science 37 (2002) 1959-1965, J. Phys. Chem. A 2009, 113, 15006-15015, Ind. Eng. Chem. Res. 48, 4334-4339, 2009 disclose UV-visible diffuse reflectance spectra of TS-1, wherein the peak at 220 nm represents the bonding of titanium-oxygen-silicon, and the peak at 330 nm represents the bonding of titanium-oxygen-titanium. The higher titanium content results in more significant peak at 330 nm. The MFI structure is based on the bonding of titanium-oxygen-silicon, and thus the conventional technology focused on the reduction of the bonding of titanium-oxygen-titanium, and developed the methods for lowering the titanium content. However, the lower titanium content results in fewer activity spots on the TS-1 molecular sieve and lower catalyst activity. The particle size of the conventional molecular sieve is about 0.2 μm. However, such catalyst applied in the industry (such as the preparation of cyclohexanone oxime from cyclohexanone, ammonia and hydrogen peroxide) needs to be improved.

Thus, the technologies have been developed to enlarge the particle size of the molecular sieve. U.S. Pat. Nos. 5,500,199, 6,106,803 and 6,524,984 disclose that small particles are aggregated by an inorganic adhesive agent, and then spray-dried. The particle size of the catalyst in these methods is enlarged; however, the active site of the catalyst is covered by the adhesive agent, the reactivity of the catalyst is decreased, and the amount of the catalyst in the reaction needs to be increased.

Hence, it is an urgent issue to develop a method for preparing a titanium-silicalite molecular sieve with a large particle size and high activity so as to facilitate the recovery of the molecular sieve, improve the usage efficiency of hydrogen peroxide, and favor the application in the industry.

SUMMARY OF THE INVENTION

The present invention provides a method for preparing a large-sized titanium-silicalite molecular sieve. The method includes the steps of preparing a mixture of a titanium source, a silicon source and a template agent; heating the mixture to form a gel mixture; mixing a colloidal silica with the gel mixture; heating the gel mixture mixed with the colloidal silica in a water bath; and calcining the gel mixture mixed with the colloidal silica.

The present invention further provides method for preparing cyclohexanone oxime. The method includes the step of performing a reaction of cyclohexanone, ammonia and hydrogen peroxide in the presence of a large-sized titanium-silicalite molecular sieve of the present invention and a solvent.

Specifically, in the present invention, the silicon source and the titanium source were mixed at the low temperature and under nitrogen sealing, added with a template agent solution (alcohol solution or aqueous solution), and added with water drop by drop. After removing the alcohol and adding the colloidal silica, the gel mixture mixed with the colloidal silica is sealed in a stainless steel can to be heated in a water bath. After heating in the water bath, the solid is separated from the liquid to obtain the gel mixture mixed with the colloidal silica.

In the present invention, the silicon source may be a silicate or polyethoxysiloxane. The silicate may be tetraalkyl silicate such as tetramethyl silicate, tetraethyl silicate, tetrapropyl silicate or tetrabutyl silicate. The polyethoxysiloxane may be ES-28 (n=1~2), ES-32 (n=3~4) or ES-40 (n=4~5).

In the present invention, the titanium source may be a tetraalkyl titanate. The tetraalkyl titanate is tetraethyl titanate, tetraisopropyl titanate or tetrabutyl titanate. Further, the molar ratio of the titanium source to the silicon source ranges from 0.0167:1 to 0.1:1; and the molar ratio of the template agent to the silicon source ranges from 0.1:1 to 0.5:1.

In the present invention, the template agent includes tetrapropylammonium hydroxide in a solvent comprising at least one alcohol or an aqueous solution. For example, the tetrapropylammonium hydroxide is dissolved in an alcohol or water for the anion exchange resin process. The alcohol is a linear or branched alcohol having 1 to 8 carbons such as methanol, ethanol, isopropanol, n-butanol or tert-butanol. The alcohol concentration of the template agent solution may be 5 wt % to 50 wt %.

In the present invention, the colloidal silica may be silicon dioxide gel solution such as Ludox AS-40, Ludox AS-30, Ludox TM-40, Ludox TM-50, Ludox AM-30, Ludox HS-30, Ludox HS-40 (DuPont) or SNOWTEX-40, SNOWTEX-50, SNOWTEX-C, SNOWTEX-N, SNOWTEX-20L, SNOWTEX-ZL, SNOWTEX-UP (Nissan Chemical Industries, Ltd.) In the present invention, the weight ratio of the colloidal silica to water ranges from 1:0.1 to 80:1; and the weight ratio of the colloidal silica to the gel mixture ranges from 0.001:1 to 0.2:1.

Since the gel mixture is added with the colloidal silica, the average particle size of the titanium-silicalite molecular sieve is more than 10 micrometers, the particle size distribution is centralized, and the titanium content in the titanium-silicalite molecular sieve is decreased.

In the present invention, the reaction is performed at 1 atm or higher pressure, and 40 to 110° C., preferably 50 to 90° C. In the reaction, the amount of the titanium-silicalite molecular sieve is 0.1 to 10 wt % of the total amount of reactants. Preferably, the amount of the titanium-silicalite molecular sieve is 1 to 5 wt % of the total amount of reactants. The molar ratio of ammonia to cyclohexanone ranges from 1.2:1 to 2:1, preferably 1.4:1 to 1.8:1; and the molar ratio of hydrogen peroxide to cyclohexanone ranges from 0.7:1 to 2.0:1, preferably 1.0:1 to 1.5:1. The concentration of hydrogen peroxide is 30 wt % to 50 wt %. The hydrogen peroxide is gradually added in the reaction. The preparation of cyclohexanone oxime may be performed in the presence of a solvent such as a polar solvent, which may be one or more selected from the group consisting of an alcohol, a ketone and water. Preferably, the solvent is an alcohol. More preferably, the solvent is tert-butanol.

In the present invention, the formation of titanium-titanium oxide is avoided, and the titanium-silicalite molecular sieve has a large particle size and the centralized particle distribution. The preparation of cyclohexanone oxime using the titanium-silicalite molecular sieve as the catalyst results in high conversion rate of cyclohexanone, high selectivity of cyclohexanone oxime and high usage efficiency of hydrogen peroxide.

DETAILED DESCRIPTION OF THE INVENTION

Figure 1:
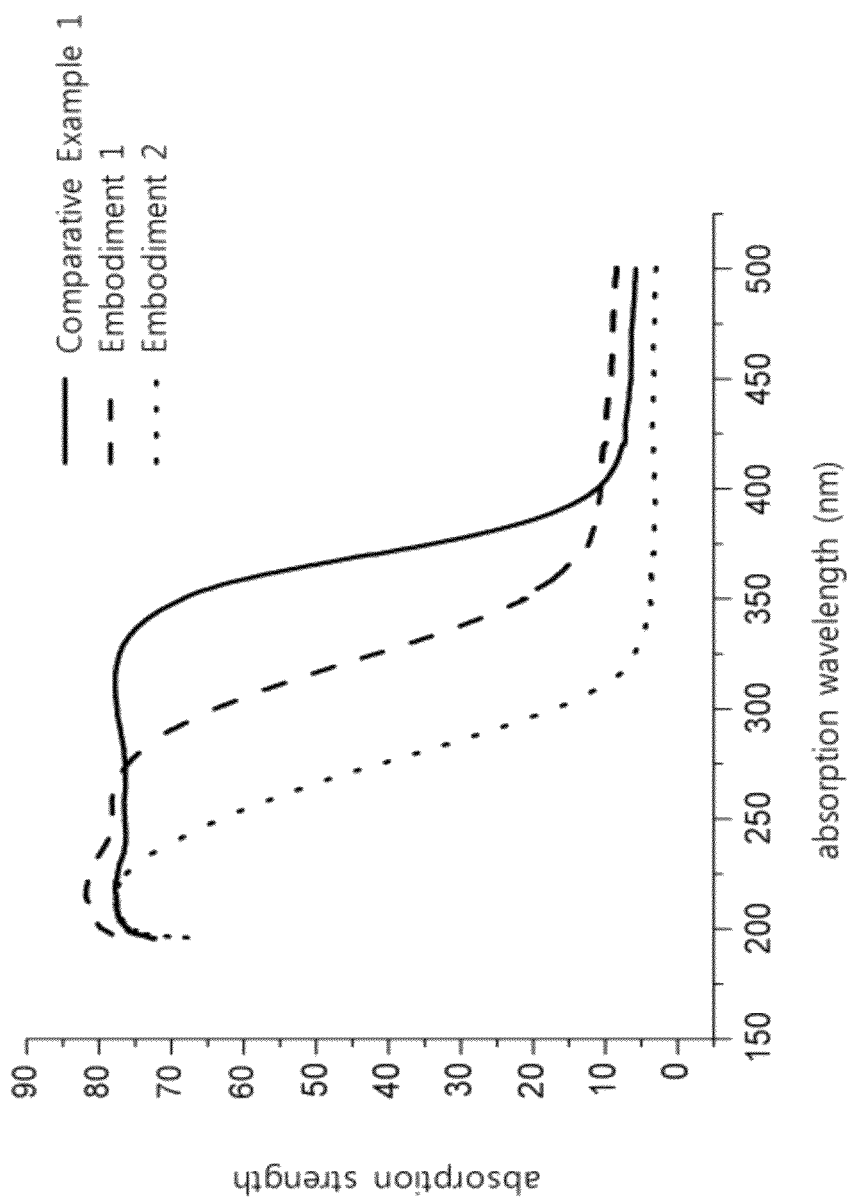
FIG. 1 is a diagram showing UV reflection spectra of Comparative Example 1, Embodiment 1 and Embodiment 2.

The following specific embodiments are provided to illustrate the disclosure of the present invention. These and other advantages and effects can be easily understood by those skilled in the art after reading the disclosure of this specification.

COMPARATIVE EXAMPLE 1

A flask (500 ml) was nitrogen sealed under vacuum. 1.98 g of tetrabutyl titanate was added into the flask, and then cooled down to 5° C. Then, 30 g of tetraethyl silicate was dropped into the flask, and then stirred for 1 hour. 56 g (20 wt %) of tetrapropylammonium hydroxide solution was dropped into the flask, and then stirred for 1 hour. After the temperature of the reaction system was back to the room temperature, the mixture was stirred for 1 hour. Then, the mixture was heated at 85° C. for 2 hours, then added with 80 g of water and stirred for 1 hour, so as to form the titanium-silicon template agent gel mixture. The gel mixture was sealed in a stainless steel can having a Teflon liner, and was heated at 180° C. for 120 hours. Then, the solid was separated from the liquid, and was cleaned with pure water to be neutral. The solid was dried at 100° C., and calcined at 550° C. for 8 hours, so as to obtain the catalyst sample 1 (titanium-silicalite molecular sieve having the average particle size: 4.52 um, and the median particle size ($d_{50}$): 2.53 um).

Embodiment 1

A flask (500 ml) was nitrogen sealed under vacuum. 1.98 g of tetrabutyl titanate was added into the flask, and then cooled down to 5° C. Then, 30 g of tetraethyl silicate was dropped into the flask, and then stirred for 1 hour. 56 g (20 wt %) of tetrapropylammonium hydroxide solution was dropped into the flask, and then stirred for 1 hour. After the temperature of the reaction system was back to the room temperature, the mixture was stirred for 1 hour. Then, the mixture was heated at 85° C. for 2 hours; meanwhile, a dispersion solution was prepared (10.8 g of colloidal silica solution (40 wt %) was dispersed in 73.5 g water). The titanium-silicon template agent gel mixture was mixed with the dispersion solution and stirred for 1 hour. The gel mixture mixed with the colloidal silica was sealed in a stainless steel can having a Teflon liner, and was heated at 180° C. for 120 hours. Then, the solid was separated from the liquid, and was cleaned with pure water to be neutral. The solid was dried at 100° C., and calcined at 550° C. for 8 hours, so as to obtain the catalyst sample 2 (titanium-silicalite molecular sieve having the average particle size: 17.78 um, and the median particle size ($d_{50}$): 15.28 um).

Embodiment 2

A flask (500 ml) was nitrogen sealed under vacuum. 1.98 g of tetrabutyl titanate was added into the flask, and then cooled down to 5° C. Then, 30 g of tetraethyl silicate was dropped into the flask, and then stirred for 1 hour. 56 g (20 wt %) of tetrapropylammonium hydroxide in isopropanol solution was dropped into the flask, and then stirred for 1 hour. Then, the reaction system was added slowly with 44.8 of water, and stirred for 1 hour. After the temperature of the reaction system was back to the room temperature, the mixture was stirred for 1 hour. The alcohol was removed at 85° C. for 2 hours. Meanwhile, 10.8 g of Ludox AS-40 (colloidal silica solution) was dispersed in 73.5 g of water to form a dispersion solution. The titanium-silicon template agent gel mixture was mixed with the dispersion solution and stirred for 1 hour. The gel mixture mixed with the colloidal silica was sealed in a stainless steel can having a Teflon liner, and was heated at 180° C. for 120 hours. Then, the solid was separated from the liquid, and was cleaned with pure water to be neutral. The solid was dried at 100° C., and calcined at 550° C. for 8 hours, so as to obtain the catalyst sample 3 (titanium-silicalite molecular sieve having the average particle size: 14.13 um, and the median particle size ($d_{50}$): 11.77 um).

Embodiments 3-6

These embodiments were similar to Embodiment 2 except that 14.4 g of Ludox AM-30, 10.8 g of Ludox HS-40, 8.64 g of Ludox TM-50 or 14.4 g of Ludox SM-30 (colloidal silica solution) was dispersed to form a dispersion solution, so as to obtain the catalyst samples 4-7 (titanium-silicalite molecular sieve having the average particle size: 10.54-18.60 um, and the median particle size ($d_{50}$): 9.35-13.03 um).

Embodiments 7-12

These embodiments were similar to Embodiment 2 except that 1.08 g, 2.16 g, 3.93 g, 5.70 g, 7.47 g or 9.24 g of Ludox AS-40 (colloidal silica solution) was added, so as to obtain the catalyst samples 8-13 (titanium-silicalite molecular sieve having the average particle size: 11.19-14.80 um, and the median particle size ($d_{50}$): 8.92-10.84 um).

Embodiments 13-14

These embodiments were similar to Embodiment 1 except that 1.22 or 7.33 g of tetrabutyl titanate was used, so as to obtain the catalyst samples 13-14 (titanium-silicalite molecular sieve having the average particle size: 12.7-18.7 um, and the median particle size ($d_{50}$): 11.3-14.1 um).

TEST EXAMPLE 1

The titanium-silicalite molecular sieves prepared from Comparative Example 1 and Embodiments 1-14 were respectively used as the catalyst for the preparation of cyclohexanone oxime, and the activity of the titanium-silicalite molecular sieves was determined.

0.55 g of the catalyst was placed in a flask, added with 5 g of cyclohexanone and 28% ammonia. The reaction system was equipped with a condensation tube and a stirring device. The temperature of the reaction system was heated to 60° C., and then 5.43 g of 35 wt % hydrogen peroxide solution was gradually added to perform the preparation of cyclohexanone oxime. After 1 hour upon completing the introduction of hydrogen peroxide, the catalyst was separated from the reaction solution. Then, the reaction solution was analyzed by gas chromatography and a titrator. The results were shown in Table 1.

TABLE 1

|  | $X_K$ | $S_{OX}$ | $X_H$ | $S_H$ | Average particle size (um) |
|---|---|---|---|---|---|
| Comparative Example 1 | 99.71 | 98.27 | 99.07 | 89.83 | 4.52 |
| Embodiment 1 | 98.62 | 98.35 | 99.02 | 89.88 | 17.78 |
| Embodiment 2 | 99.90 | 99.15 | 98.98 | 91.25 | 14.13 |
| Embodiment 3 | 99.40 | 99.80 | 98.94 | 91.17 | 10.86 |
| Embodiment 4 | 99.97 | 99.51 | 99.15 | 91.60 | 10.54 |
| Embodiment 5 | 99.41 | 99.00 | 99.10 | 90.53 | 16.74 |
| Embodiment 6 | 98.49 | 99.10 | 99.10 | 90.53 | 18.60 |
| Embodiment 7 | 99.91 | 99.01 | 99.19 | 90.60 | 13.19 |
| Embodiment 8 | 99.71 | 99.03 | 98.90 | 91.07 | 11.19 |
| Embodiment 9 | 99.96 | 98.77 | 98.96 | 90.97 | 11.47 |
| Embodiment 10 | 99.80 | 99.67 | 98.86 | 91.74 | 12.44 |
| Embodiment 11 | 99.78 | 98.68 | 98.78 | 91.00 | 11.71 |
| Embodiment 12 | 99.43 | 97.47 | 98.10 | 89.52 | 14.80 |
| Embodiment 13 | 98.94 | 98.53 | 99.36 | 89.51 | 12.70 |
| Embodiment 14 | 99.80 | 95.19 | 98.89 | 87.19 | 18.70 |

$X_K$: conversion rate of cyclohexanone = moles of consumed cyclohexanone/initial moles of cyclohexanone × 100%
$S_{OX}$: selectivity of cyclohexanone oxime = moles of produced cyclohexanone oxime/moles of consumed cyclohexanone × 100%
$X_H$: conversion rate of hydrogen peroxide = moles of consumed hydrogen peroxide/initial moles of hydrogen peroxide × 100%
$S_H$: selectivity of hydrogen peroxide = moles of produced cyclohexanone oxime/moles of consumed hydrogen peroxide × 100%

TEST EXAMPLE 2

FIG. 1 shows the diffused reflection UV spectra of the titanium-silicalite molecular sieves prepared from Comparative Example 1 and Embodiments 1-2. As shown in FIG. 1, the addition of the colloidal silica reduced the titanium content outside the sieve skeleton, and the template agent solution such as tetrapropylammonium hydroxide in an alcohol solution further significantly reduced the titanium content outside the sieve skeleton.

TEST EXAMPLE 3

Figure 2:
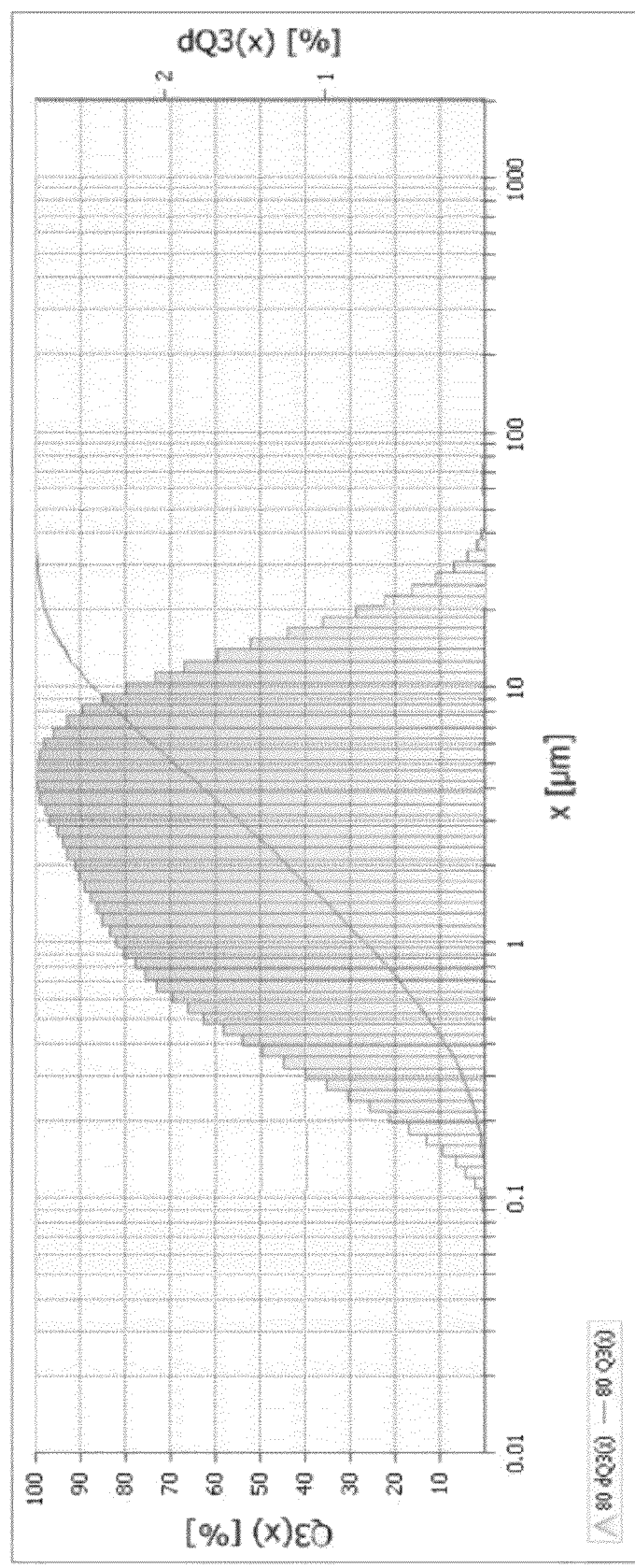
FIG. 2 shows the analysis result of the particle size of the titanium-silicalite molecular sieve in Comparative Example 1.
Figure 3:
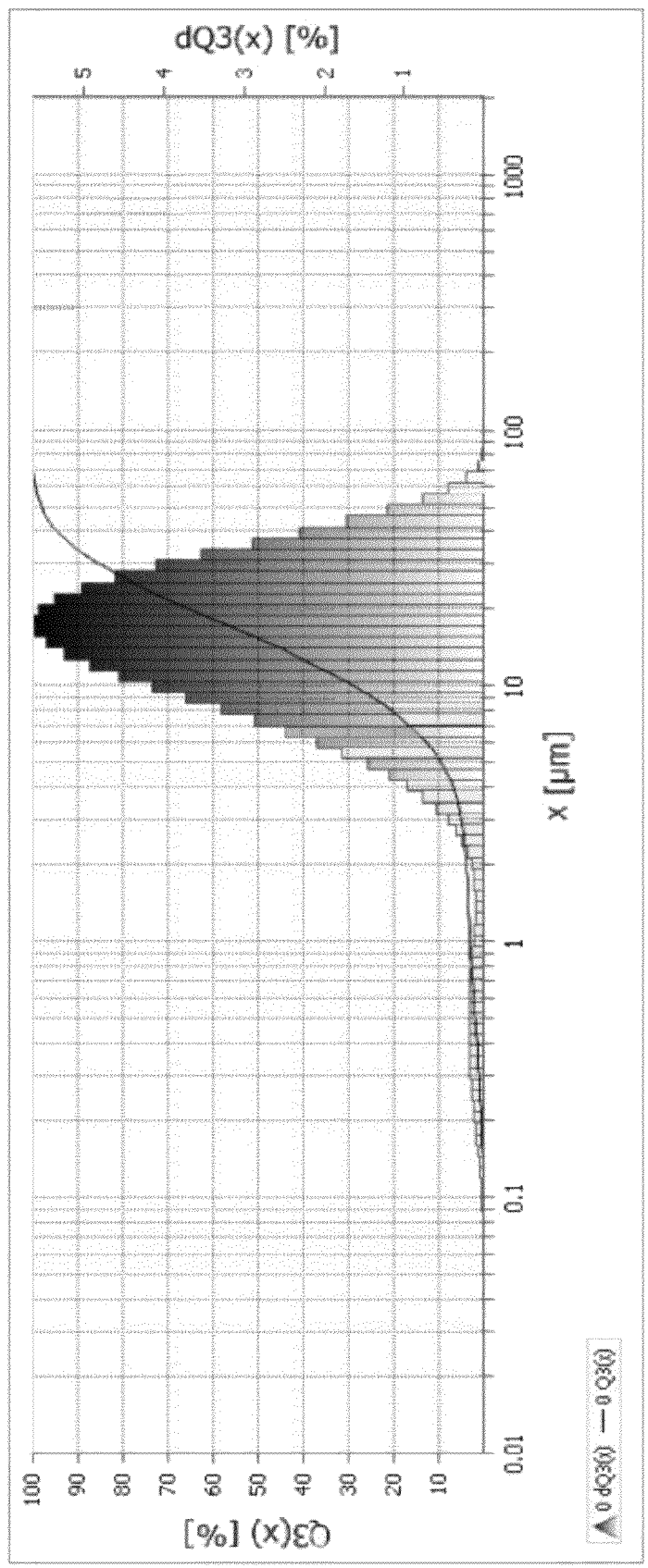
FIG. 3 shows the analysis result of the particle size of the titanium-silicalite molecular sieve in Embodiment 1.
Figure 4:
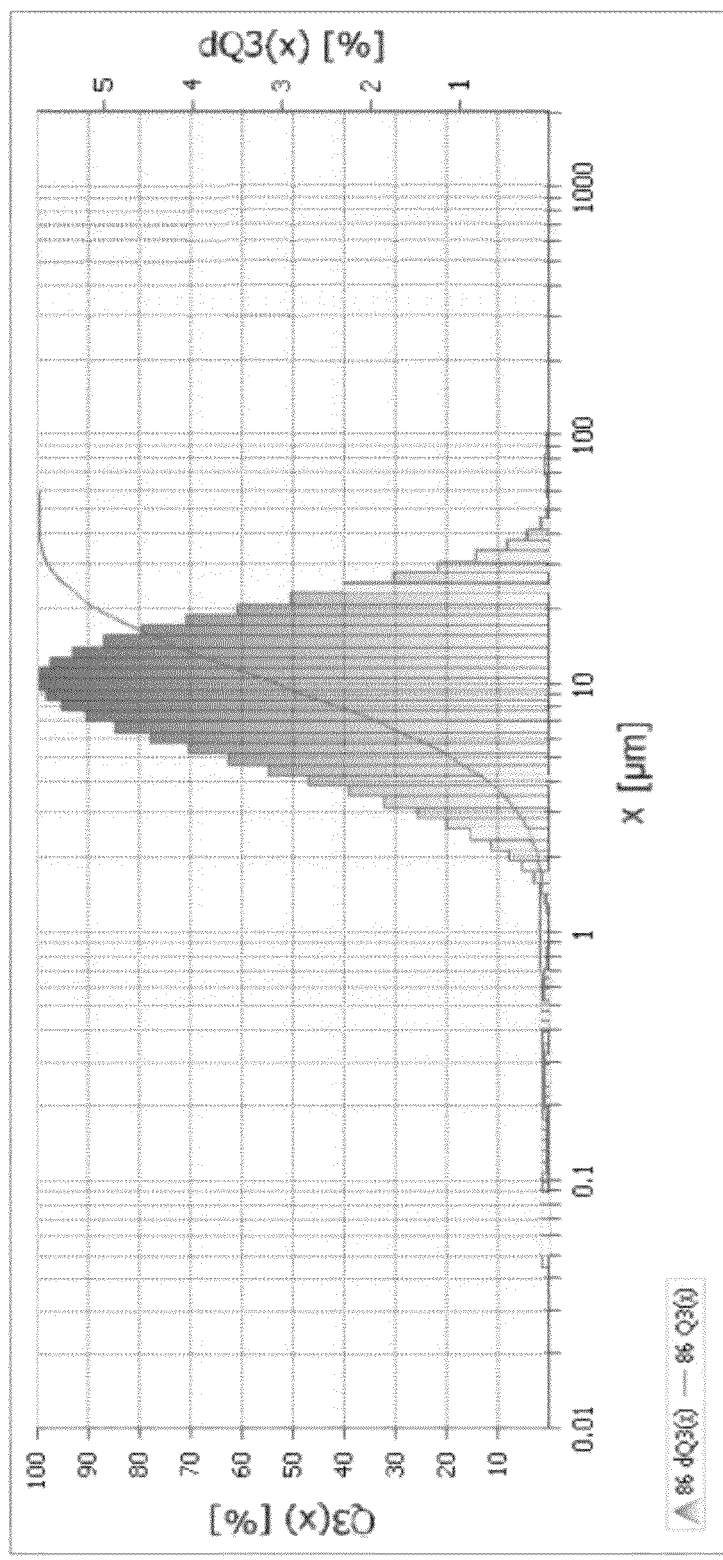
FIG. 4 shows the analysis result of the particle size of the titanium-silicalite molecular sieve in Embodiment 2.

The particle size of the titanium-silicalite molecular sieves prepared from Comparative Example 1 and Embodiments 1-2. The results were shown in FIG. 2 to FIG. 4, wherein x was the particle size (um); Q3(x) % was the ratio of the volume of the particles having the particle size smaller than x to the volume of the total particles; and dQ3(x) % was the value of Q3(x) differentiated by x.

Accordingly, the present invention provides a method for preparing a large-sized titanium-silicalite molecular sieve, wherein the particle size distribution is centralized, and the large-sized titanium-silicalite molecular sieve has high catalyst activity. The present invention further provides a method for preparing cyclohexanone oxime using the large-sized titanium-silicalite molecular sieve of the present invention as the catalyst, resulting in high selectivity, high conversion rate, high usage of hydrogen peroxide and easy recovery. In light of the diffused reflection UV spectra, the peak at 330 nm was significantly inhibited, indicating the maintenance of catalyst activity.

The invention has been described using exemplary preferred embodiments. However, it is to be understood that the scope of the invention is not limited to the disclosed embodiments. On the contrary, it is intended to cover various modifications and similar arrangements. The scope of the claims, therefore, should be accorded the broadest interpretation so as to encompass all such modifications and similar arrangements.

What is claimed is:

1. A method for preparing a large-sized titanium-silicalite molecular sieve, comprising the steps of:
   preparing a mixture of a titanium source, a silicon source and a template agent;
   heating the mixture to form a gel mixture;
   mixing a colloidal silica with the gel mixture;
   heating the gel mixture mixed with the colloidal silica in a water bath; and
   calcining the gel mixture mixed with the colloidal silica.

2. The method of claim 1, wherein the titanium source is tetraalkyl titanate.

3. The method of claim 1, wherein the silicon source is tetraalkyl silicate or polyethoxysiloxane.

4. The method of claim 1, wherein the template agent is tetrapropylammonium hydroxide.

5. The method of claim 1, wherein the template agent includes at least one solvent, and the solvent is selected from alcohol solvents.

6. The method of claim 5, wherein the template agent includes one or more alcohol solvents selected from the group consisting of methanol, ethanol, isopropanol, n-butanol and tert-butanol.

7. The method of claim 5, wherein the gel mixture mixed with the colloidal silica is heated to remove the solvent.

8. The method of claim 1, wherein the colloidal silica is silicon dioxide gel solution.

9. The method of claim 1, wherein a molar ratio of the titanium source to the silicon source ranges from 0.0167:1 to 0.1:1; and a molar ratio of the template agent to the silicon source ranges from 0.1:1 to 0.5:1.

10. The method of claim 1, wherein an average particle size of the large-sized titanium-silicalite molecular sieve is more than 10 um.

11. The method of claim 1 further comprising preparing cyclohexanone oxime by performing a reaction of cyclohexanone, ammonia and hydrogen peroxide in the presence of said large-sized titanium-silicalite molecular sieve and a solvent.

12. The method of claim 11, wherein a molar ratio of the ammonia to the cyclohexanone ranges from 1.2:1 to 2:1.

13. The method of claim 11, wherein a mole ratio of the hydrogen peroxide to the cyclohexanone is in a range from 0.7:1 to 2.0:1.

14. The method of claim 11, wherein the solvent is a polar solvent, and the polar solvent is one or more selected from the group consisting of an alcohol, a ketone and water.

15. The method of claim 11, wherein the solvent is tert-butanol.

16. The method of claim 11, wherein an amount of the titanium-silicalite molecular sieve is 0.1 to 10 wt % of a total weight of the cyclohexanone, the ammonia and the hydrogen peroxide.

\* \* \* \* \*